US007828796B2

(12) United States Patent
Wong et al.

(10) Patent No.: US 7,828,796 B2
(45) Date of Patent: Nov. 9, 2010

(54) METHOD FOR CREATING A CHANNEL THROUGH AN OCCLUSION AND APPARATUS THEREFOR

(75) Inventors: Christine Wong, Toronto (CA); Gareth Davies, Toronto (CA); Ramsey Leung, Etobicoke (CA); Mark Mosley, Oakville (CA)

(73) Assignee: Baylis Medical Company Inc., Montréal (CA)

( * ) Notice: Subject to any disclaimer, the term of this patent is extended or adjusted under 35 U.S.C. 154(b) by 1002 days.

(21) Appl. No.: 11/520,754

(22) Filed: Sep. 14, 2006

(65) Prior Publication Data

US 2007/0066975 A1  Mar. 22, 2007

Related U.S. Application Data

(60) Provisional application No. 60/596,297, filed on Sep. 14, 2005.

(51) Int. Cl.
*A61B 18/12* (2006.01)
(52) U.S. Cl. .............................. 606/45; 606/41; 606/46; 607/101
(58) Field of Classification Search ............. 606/45–46, 606/39
See application file for complete search history.

(56) References Cited

U.S. PATENT DOCUMENTS

| 5,047,026 | A | * | 9/1991 | Rydell | .......................... 606/48 |
| 5,605,162 | A | * | 2/1997 | Mirzaee et al. | ............. 600/585 |
| 6,530,923 | B1 | * | 3/2003 | Dubrul et al. | ................. 606/45 |
| 6,562,031 | B2 | * | 5/2003 | Chandrasekaran et al. | .... 606/41 |
| 2004/0073243 | A1 | * | 4/2004 | Sepetka et al. | .............. 606/159 |

OTHER PUBLICATIONS

Suhonen M. et al. Recanalization of arterial occlusions using a specially designed steering catheter. European Radiology: 2, 264-265(1992).*

* cited by examiner

*Primary Examiner*—Linda C Dvorak
*Assistant Examiner*—Jaymi Della

(57) ABSTRACT

A method for creating a channel through an occlusion located in a substantially elongated body vessel of a patient, The method uses a channel creating apparatus defining an apparatus distal end portion insertable into the body vessel, the channel creating apparatus including an energy delivery component operatively coupled to the apparatus distal end portion for delivering energy substantially adjacent the apparatus distal end portion. The method includes: inserting the apparatus distal end portion into the body vessel; creating a channel first portion through the occlusion harder section using, at least in part, a delivery of energy into the occlusion harder portion; and creating a channel second portion through the occlusion softer portion by pushing the apparatus distal end portion through at least a portion of the occlusion softer portion substantially without delivering energy into the occlusion softer portion.

20 Claims, 8 Drawing Sheets

METHOD FOR CREATING A CHANNEL THROUGH AN OCCLUSION AND APPARATUS THEREFOR

This application also claims the benefit of U.S. provisional patent application Ser. No. 60/596,297, filed Sep. 14, 2005. The contents of all these US Patent Applications is hereby incorporated by reference in their entirety.

FIELD OF THE INVENTION

The present invention relates generally to methods and devices usable to create channels in the body of a patient. More specifically, the present invention is concerned with a method for creating a channel through an occlusion and an apparatus therefor.

BACKGROUND OF THE INVENTION

There are currently two general classes of methods used to create channels through an occlusion, for example an occlusion located in a blood vessel of a patient.

The first class of methods uses a guide wire mechanically pushed through the occlusion. A major disadvantage of such methods resides in that the wire dimensions, and hence the wire rigidity, is limited by the dimensions of the vessels though which the wire must be inserted to reach the occlusion and by currently available materials. Therefore, it often occurs that a specific occlusion has a portion that is too hard to allow pushing the wire therethrough.

For example, many occlusions located in blood vessels include a calcified or fibrous cap at the ends thereof, the cap being in some cases too hard to allow penetration by the wire. The remaining portions of the occlusions are typically relatively soft and are relatively easily penetrated by existing mechanical guide-wires.

In another class of methods, energy, for example radio-frequency energy, is delivered into the occlusion and a device delivering the energy is advanced through a channel thereby created. However, applying energy, while allowing to go through relatively hard occlusions, is often risky as the energy may vaporize or liquefy the wall of the blood vessel, which may thereby be injured and cause complications that require an emergency surgery, or even death.

Due to this risk, many devices that utilize energy to go through an occlusion include means for ensuring that the energy is not delivered through the vessel wall. For example, an optical sensor is used to acquire information related to the composition of the tissue into which the energy is provided. If the tissue is determined not to be a tissue through which the channel should be created, the delivery of energy is stopped. However, such devices are relatively complex, relatively expensive, relatively complex to operate and relatively large, which make them impractical or unsuitable for many interventions.

In addition, many currently existing devices used to create channels within the body have a substantially fixed shape, for example a substantially curved or a substantially rectilinear shape, when no external force is applied on the device. These devices are therefore relatively hard to direct to create channels having a predetermined shape. Also, these devices may be difficult to advance in a desired direction when reaching bends or bifurcations within the body vessels.

Current devices are intended to use either radiofrequency or mechanical energy to traverse occlusions in their entirety. Such devices would typically not be used to provide both functionalities due to, for example, the size, shape and/or other properties of the devices. For example, standard mechanical guide-wires are not structured to for delivery of electrical energy and current radio-frequency devices are typically not suitable for mechanical perforation. In addition, many clinicians may avoid using current radio-frequency devices to traverse occlusions due to the fact that they prefer the 'feel' of a standard guide-wire, such as those they've used previously for such procedures.

Against this background, there exists a need in the industry to provide novel methods and apparatuses for creating a channel through an occlusion. An object of the present invention is therefore to provide such a method and an apparatus.

SUMMARY OF THE INVENTION

In a first broad aspect, the invention provides a method for creating a channel through an occlusion located in a substantially elongated body vessel of a patient, the occlusion including an occlusion harder portion extending substantially longitudinally relative to the body vessel and an occlusion softer portion extending substantially longitudinally relative to the body vessel, the occlusion softer portion being located substantially adjacent to and substantially coaxial with the occlusion harder portion, the occlusion harder portion being substantially harder than the occlusion softer portion, the method using a channel creating apparatus defining an apparatus distal end portion insertable into the body vessel, the channel creating apparatus including an energy delivery component operatively coupled to the apparatus distal end portion for delivering energy substantially adjacent the apparatus distal end portion. The method includes:

inserting the apparatus distal end portion into the body vessel;

positioning the apparatus distal end portion substantially adjacent the occlusion harder portion and creating a channel first portion through the occlusion harder portion, creating the channel first portion including delivering the energy into the occlusion harder portion using said energy delivery component; and positioning the apparatus distal end portion substantially adjacent the occlusion softer portion and creating a channel second portion through the occlusion softer portion by pushing the apparatus distal end portion through at least a portion of the occlusion softer portion, said channel second portion being created substantially without using the energy delivery component to deliver energy into the occlusion softer portion.

Advantageously, the proposed method improves the safety of the channel creating method as the energy is used substantially only to go through relatively hard portions of the occlusion. Also, the use of energy in creating the channel allows an intended user to create channels in portions of the occlusion through which channel creation without using energy is difficult or impossible to perform.

In some embodiments of the invention, the proposed method is performed using relatively small apparatuses, for example apparatuses having a relatively small diameter, which are therefore relatively easily introduced in relatively small vessels. Also, such apparatuses are relatively easily introduced into a catheter having a distal end located substantially adjacent the occlusion so as to be relatively easily replaced by alternative conventional apparatuses is desired.

In addition, the proposed method is relatively easily performed using apparatuses whose mechanical properties are substantially similar to conventional devices, for example standard mechanical guide wires, and are therefore relatively easily used by conventionally trained medical personnel.

In addition, the proposed method is relatively easily performed using relatively simple, efficient and cost-effective devices.

In another broad aspect, the invention provides a method for creating a channel through an occlusion located in a substantially elongated body vessel of a patient. The occlusion includes an occlusion harder portion extending substantially longitudinally relative to the body vessel and an occlusion softer portion extending substantially longitudinally relative to the body vessel, the occlusion softer portion being located substantially adjacent to and substantially coaxial with to the occlusion harder portion. The method uses a channel creating apparatus defining an apparatus distal end portion insertable into the body vessel, the channel creating apparatus including an energy delivery component operatively coupled to the apparatus distal end portion for delivering energy substantially adjacent the apparatus distal end portion, the energy delivery component being selectively operable in an energy delivering state and in a deactivated state. In the energy delivering state, the energy is delivered substantially adjacent the apparatus distal end portion, and in the deactivated state, the energy is substantially not delivered substantially adjacent the apparatus distal end portion. The method includes:

inserting the apparatus distal end portion into the body vessel;

positioning the apparatus distal end portion substantially adjacent the occlusion harder portion and creating a channel first portion through the occlusion harder portion by operating the energy delivery component in the energy delivering state and delivering the energy into the occlusion harder portion; and positioning the apparatus distal end portion substantially adjacent the occlusion softer portion and creating a channel second portion through the occlusion softer portion by operating the energy delivery component in the deactivated state and substantially simultaneously pushing the apparatus distal end portion through at least a portion of the occlusion softer portion.

In another broad aspect, the invention provides a method for creating a channel through an occlusion located in a substantially elongated body vessel of a patient, the occlusion including an occlusion first portion extending substantially longitudinally relative to the body vessel and an occlusion second portion extending substantially longitudinally relative to the body vessel, the occlusion second portion being located substantially adjacent to and coaxial with the occlusion first portion, the method using a channel creating apparatus defining an apparatus distal end portion insertable into the body vessel and an apparatus proximal portion substantially longitudinally opposed to the apparatus distal end portion, the channel creating apparatus including an energy delivery component operatively coupled to the apparatus distal end portion for delivering energy substantially adjacent the apparatus distal end portion, the method comprising:

inserting the apparatus distal end portion into the body vessel;

positioning the apparatus distal end portion substantially adjacent to the occlusion first portion and creating a channel first portion through the occlusion first portion by delivering said energy into the occlusion first portion via said energy delivery component while advancing the apparatus distal end portion; and attempting to advance the apparatus distal end portion at least partially through the occlusion second portion by applying longitudinal force to said apparatus proximal portion to create a channel second portion through the occlusion second portion substantially without delivering energy into the occlusion second portion via said energy delivery component.

In a variant, the occlusion second portion is substantially softer relative to the occlusion first portion.

Other objects, advantages and features of the present invention will become more apparent upon reading of the following non-restrictive description of certain embodiments thereof, given by way of example only with reference to the accompanying drawings.

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1A:
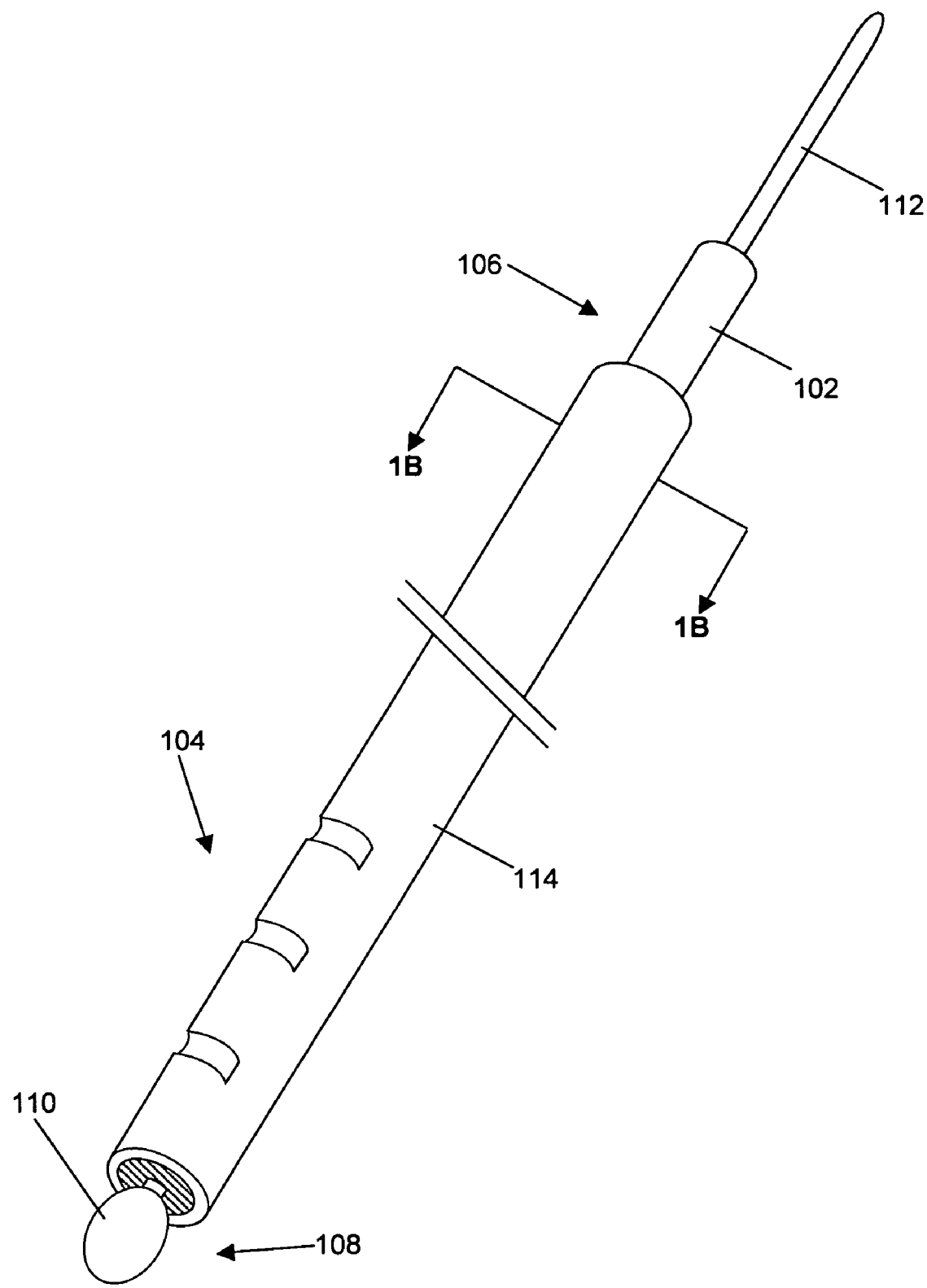
FIG. 1A, in a perspective view, illustrates an apparatus for creating a channel in an occlusion in accordance with an embodiment of the present invention.

With specific reference now to the drawings in detail, it is stressed that the particulars shown are by way of example and for purposes of illustrative discussion of embodiments of the present invention only, and are presented in the cause of providing what is believed to be the most useful and readily understood description of the principles and conceptual aspects of the invention.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purposes of this description, proximal indicates next to or nearer to the user, and distal indicates further away from the user.

Apparatus Structure

As illustrated in FIG. 1, one embodiment of an apparatus 100 of the present invention may generally comprise a substantially elongate member 102 having a distal region 104 and a proximal region 106. Distal region 104 may comprise a distal tip 108 and an energy delivery component 110 may be associated with distal tip 108. Energy delivery component 110 may be any means for delivering energy, such as, by non-limiting example, a radio-frequency energy delivery component or a laser component, among other possibilities. In the embodiment shown in FIG. 1, apparatus 100 further comprises an actuator 112 for directing at least a portion of distal region 104 in a desired direction.

Elongate member 102 may be electrically conductive and may be operable to conduct energy to distal tip 108. In such embodiments, elongate member 102 may be referred to as a core wire. In the illustrated embodiments, the core wire is at least partially covered with an electrically insulating material 114 for substantially preventing conduction of electrical energy to surrounding bodily tissue. In accordance with these embodiments, insulating material 114 may be made of any of a variety of electrically insulating materials and may have any suitable thickness, provided that the core wire is at least partially electrically insulated. In one particular embodiment, insulating material 114 may be at least about 0.1 mm thick. The core wire may comprise a wire that may be narrow enough to be navigated through a blood vessel. In some specific embodiments, the core wire may measure about 0.2 mm to about 1.0 mm in diameter.

In alternate embodiments, insulating material 114 may be discontinuous at one or more locations along the core wire. For example, in one such embodiment, a number of discontinuities in insulating material 114, along the length of the core wire, may create a 'banded' appearance, wherein insulated regions are interleaved between electrically exposed and conductive regions. In another embodiment, a region of insulating material 114 may not completely circumscribe the core wire. For example, insulating material 114 may traverse approximately 180 degrees of the circumference of the core wire, leaving the remaining area electrically exposed. Any shape or pattern of discontinuities may be present and the invention is not intended to be limited in this regard. Discontinuities of insulating material 114 may affect the distribution of energy, for example current density, around the core wire when the core wire is used to deliver energy. Embodiments of the present invention comprising such discontinuities may be suitable for specific applications, for example, where it is desirable to deliver energy along a portion of the length of elongate member 102 or to focus the delivery of energy to a particular location or target site. In some embodiments, discontinuities in insulating material 114 may correspond, at least in part, to discontinuities in the structure of the core wire. For example, in one specific embodiment, notches, described in greater detail below, may be present in the core wire, whereby the thickness of insulating material 114 may be reduced in the vicinity of the notches.

In some embodiments, at least a portion of proximal region 106 of the core wire may be electrically exposed, such that proximal region 106 may be coupled to an electrical connector for connecting the core wire to an energy source.

In further embodiments, elongate member 102 may be made of an electrically insulating material. In such embodiments, insulating material 114 may not be required. For example, in some embodiments, elongate member 102 may be made of nylon (Pebax), polyetheretherketone (PEEK), or polypropylene, and at least one energy delivery component 110 may be attached to distal tip 108, wherein energy delivery component 110 may be operable to be electrically coupled to an energy source. In one particular embodiment, energy delivery component 110 may be electrically coupled to actuator 112, which itself may be made of an electrically conductive material and which may be capable of being electrically coupled to an energy source. Alternatively, one or more energy delivery components 110 may be attached to elongate member 102, rather than to actuator 112, they may have any size or shape and they may be present at any position along the length of elongate member 102.

In some embodiments, at least a portion of distal region 104 may be structured to prevent unwanted damage to a patient's vasculature when apparatus 100 is inserted therethrough. For example, as shown in the close-up view of FIG. 2, distal tip 108 may have a substantially atraumatic shape, for example a blunt or rounded edge, for preventing such damage as apparatus 100 is maneuvered through the vasculature. In other embodiments, distal tip 108 may be semispherical, hemispherical, spherical, flattened, or have any other shape that may be unlikely to damage tissue upon contact. Alternatively or in addition, in some embodiments, at least a portion of distal region 104 of elongate member 102 may have a reduced rigidity, relative to proximal region 106. The reduced rigidity may serve to further decrease the ability of elongate member 102 to puncture tissue, for example the tissue of a vessel wall, with the application of mechanical force, while maintaining the ability to create a channel through the soft portions of an occlusion, as described hereinbelow. This reduced rigidity may be achieved by, for example, the inclusion or substitution of a different material in the manufacture of elongate member 102, by reducing the amount of material present in at least a portion of distal region 104, or by reducing the diameter of actuator 112, in embodiments comprising an actuator. Material may be removed by, for example, using a latticework or other discontinuous structural framework, or alternatively by thinning the wall of the desired portion of elongate member 102. In one embodiment wherein elongate member 102 defines a lumen, as will be described further herein below, the wall thickness of elongate member 102 may taper in the portion of distal region 104 approaching distal tip 108. For example, the wall may taper from inside to outside, thereby maintaining a consistent outer diameter and having a changing inner diameter. Alternatively, the wall may taper from outside to inside, thereby maintaining a consistent inner diameter and having a changing outer diameter, or from both the inside and the outside thereby having the outer diameter decrease and the inner diameter increase.

As has been mentioned above, apparatus 100, as shown in the illustrated embodiments, comprises an energy delivery component 110 associated with distal tip 108. Energy delivery component 110 may be integral with one or more of elongate member 102 and actuator 112 or may be otherwise attached to distal tip 108. For example, distal tip 108 may be covered with an electrically conductive cap, the cap thus forming an energy delivery component 110 associated with distal tip 108. In embodiments wherein energy delivery component 110 is not integral with one or more of elongate member 102 and actuator 112, energy delivery component 110 may be otherwise electrically coupled to one or more of elongate member 102 and actuator 112 or to another wire operable to electrically couple energy delivery component 110 to an energy source. For example, in one embodiment, energy delivery component 110 may be continuous with actuator 112 and may be associated with distal tip 108 by being passed through elongate member 102.

Energy delivery component 110 may be larger or smaller, or may have the same diameter, as distal tip 108. In some embodiments, energy delivery component 110 is an electrode sized to be operable to generate sufficient heat in a tissue to vaporize or otherwise destroy the tissue when energy is supplied to the electrode at a sufficient power level. In one specific embodiment, the electrode may measure about 0.40 mm to about 0.43 mm in diameter and about 1.2 mm to about 1.5 mm in length. In alternate embodiments, energy delivery component 110 may comprise a means for delivering an alternate form of energy, such as, for example, thermal, optical or ultrasonic energy.

Figure 1B:
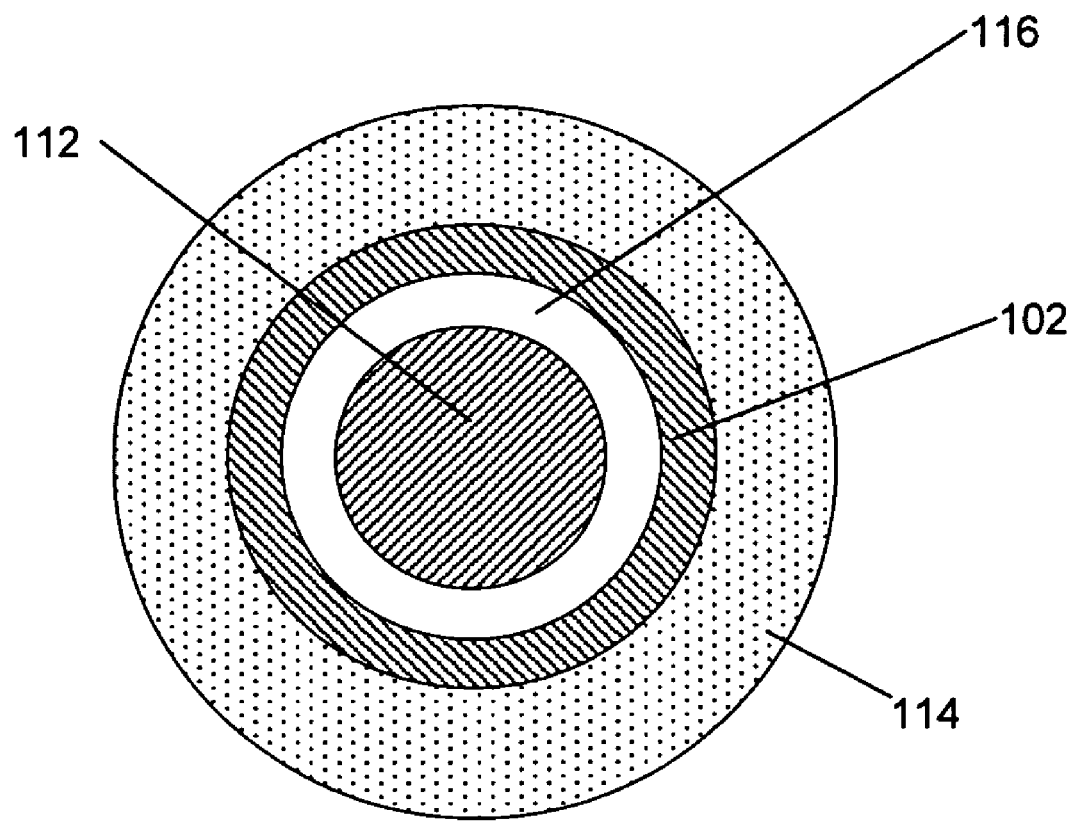
FIG. 1B, illustrates the apparatus of FIG. 1A in a front orthogonal cross-sectional view through a proximal region thereof taken along the line 1B-1B.

In the embodiment shown in FIG. 1B, as has been mentioned above, elongate member 102 defines a lumen 116 at least partially therethrough. FIG. 1B shows one embodiment of a central substantially circular lumen 116 defined by elongate member 102. In alternate embodiments, lumen 116 may have various shapes and sizes and may not be centered through elongate member 102. Alternate embodiments may not comprise a lumen; rather, elongate member 102 may be a solid structure. Lumen 116 may be sized to receive actuator 112 therein, as shown in FIG. 1. For example, in some embodiments, lumen 116 of elongate member 102 may be large enough to receive actuator 112, but may not be large enough to accommodate other wires, sensors, or the passage of fluid. In further embodiments, lumen 116 may be sized to receive actuator 112 along with one or more wires but may still not be large enough to accommodate fluid flow. In one specific embodiment, lumen 116 may measure about 0.1 mm to about 1.0 mm in diameter. The flexibility of elongate member 102 may be dependent, in part, on the wall thickness of elongate member 102, between an inner diameter defining lumen 116 and an outer diameter. In one particular embodiment, elongate member 102 may have a wall thickness measuring about 0.01 mm to about 0.2 mm in diameter. The flexibility of elongate member 102 may also depend on the outer diameter of elongate member 102. In some embodiments, elongate member 102 may have a beam strength of at least 0.001 lbf as measured by the ASTM E855-90 3-point bent test.

Figure 2:
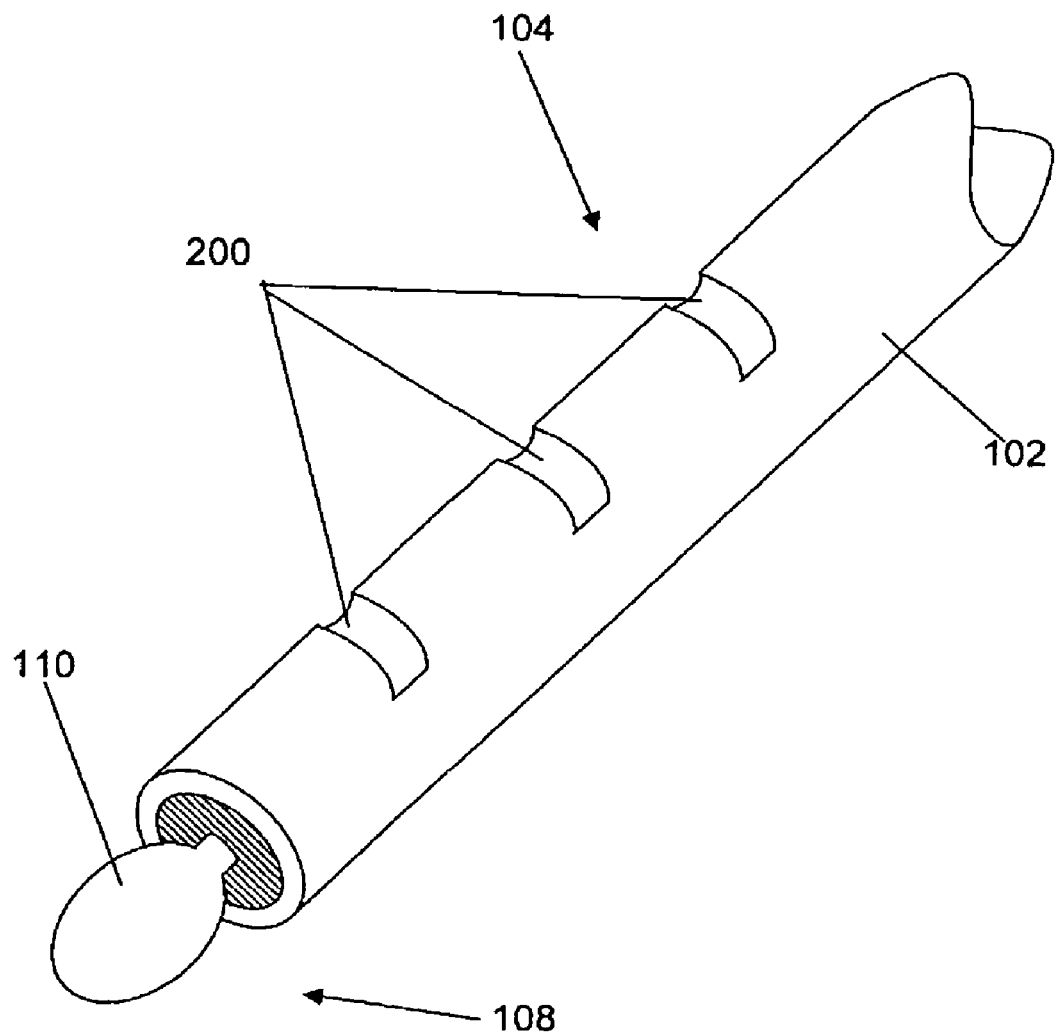
FIG. 2, in a partial perspective view, illustrates a distal region of the apparatus of FIG. 1A.
Figure 3A:
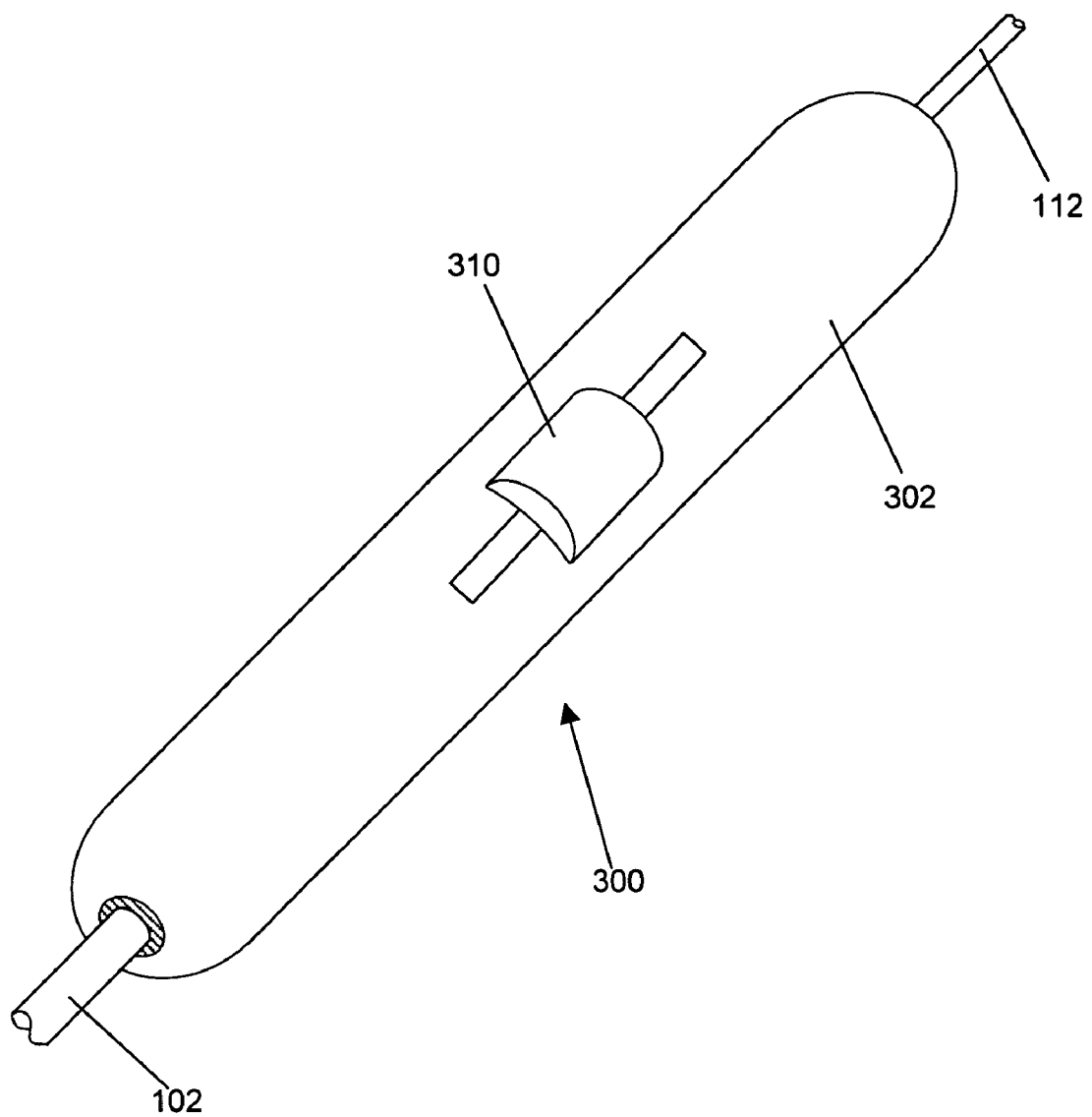
FIG. 3A, in a partial perspective view, illustrates an embodiment of a handle of an apparatus of the present invention.
Figure 3C:
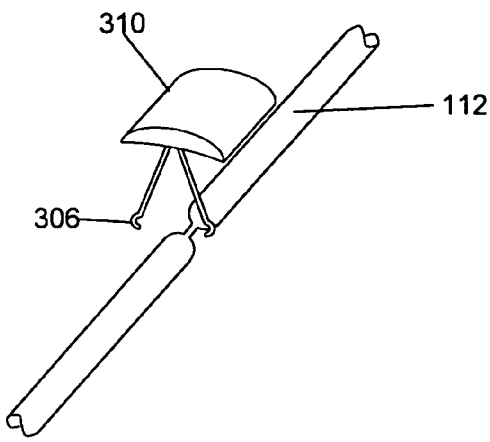
FIGS. 3C and 3D, in a perspective view, illustrate an embodiment of a securing component of an apparatus of the present invention.
Figure 3D:
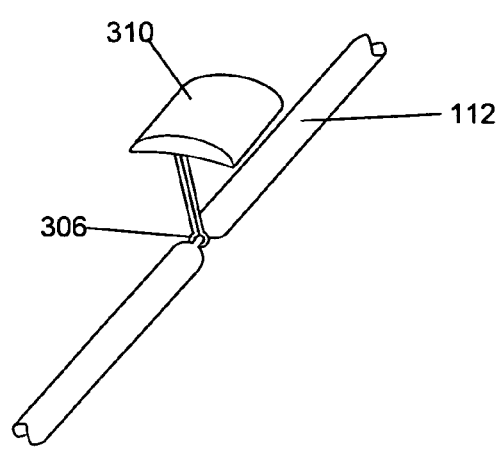
Figure 3B:
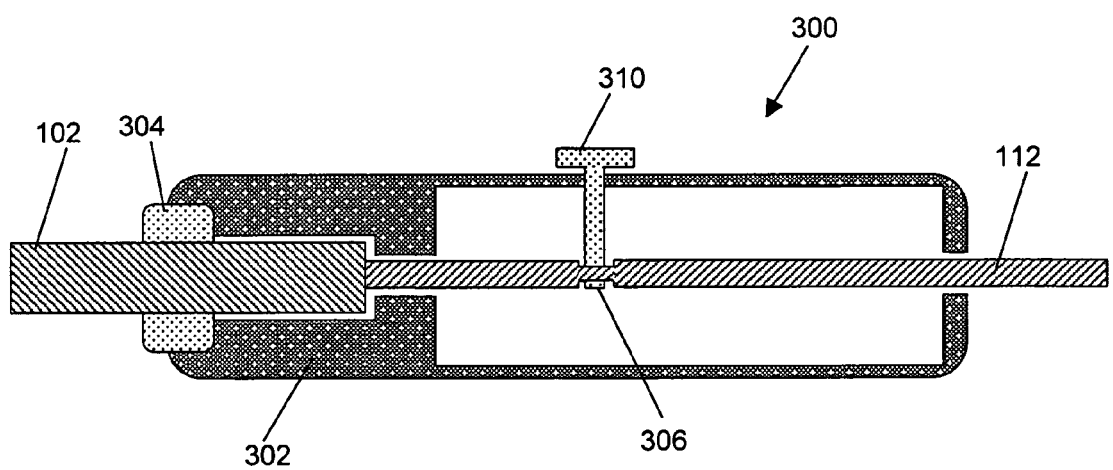
FIG. 3B, in an orthogonal side cross-sectional view taken through the line 3B-3B of FIG. 3A, illustrates the handle of FIG. 3A.

In the embodiment illustrated in FIGS. 1 and 2, actuator 112 may be a pull-wire 112 operable to direct at least a portion of distal region 104 in a desired direction. In one embodiment, actuator 112 comprises a single pull-wire disposed within lumen 116 of elongate member 102 and attached to at least one point in distal region 104 of elongate member 102. For example, the pull-wire may be attached to distal region 104 at or adjacent to distal tip 108. The pull-wire may be thin, in some embodiments, in order to allow the inner diameter of elongate member 102 to be reduced, thus potentially reducing the diameter of apparatus 100 as a whole. In one particular embodiment, the pull-wire may measure about 0.03 mm to about 0.30 mm in diameter.

The pull-wire may be attached to elongate member 102 such that manipulation of the pull-wire via the application of mechanical energy to transmit tension along the length of the pull-wire, may effect a change in elongate member 102. For example, in some embodiments, manipulation of the pull-wire may cause at least a portion of elongate member 102 to change shape. Such a change of shape may involve the adoption of a bent configuration, wherein, the term "bent" may be defined to mean having a deviation from a straight line; this may take the form of a rigid bend or a subtler curve, with one or more angles of curvature. In other embodiments, this change of shape may involve a compression, or accordion-like collapsing of elongate member 102, wherein one or more sections of elongate member 102 fold or bend backwards. Such an effect may cause the position of distal tip 108 to change, without necessarily inducing any deviation of distal tip 108 away from the longitudinal axis of distal region 104 (i.e. distal tip 108 may still point in its original direction).

In other embodiments of the present invention, actuator 112 may comprise other means for directing at least a portion of distal region 104 in a desired direction. For example, actuator 112 may comprise one or more electro-magnetic or hydraulic mechanisms for changing the shape of elongate member 102.

In alternate embodiments, apparatus 100 may comprise a pre-formed curve section. In such embodiments, distal tip 108 may be directed in a desired direction by applying torque to proximal region 106. In such embodiments, an actuator may not be required.

With respect now to the embodiment shown in FIG. 2, distal region 104 of elongate member 102 may contain one or more notches 200 to aid in a change of shape of elongate member 102 when tension is applied through the pull-wire. For the purposes of this description, notches 200 may be any regions where discontinuities are present in the wall of elongate member 102. In some embodiments, notches 200 may comprise scores, cuts, or other discontinuities in either the inner or outer surface of the wall of elongate member 102 that do not completely traverse the circumference of elongate member 102. In alternate embodiments, notches 200 may comprise regions wherein entire sections of the wall of elongate member 102 are absent. In one specific example, as shown in FIG. 2, one or more sections of the wall of elongate member 102, each section extending at least 180 degrees around the circumference of elongate member 102, are absent, which may result in a toothed or serrated appearance. Notches 200 may be present, for example, along about 5 mm to about 50 mm of the length of elongate member 102. Notches 200 may be regularly or irregularly spaced, identically, similarly or dissimilarly sized, oriented at any angle with respect to elongate member 102 and may lie at any suitable angles along elongate member 102. Notches 200 may have abrupt edges or may comprise regions where the thickness of a wall of elongate member 102 changes gradually to create a discontinuity.

As mentioned earlier, in some embodiments, notches 200 may comprise gaps, or regions where there is a total absence of material. In other embodiments, notches 200 may comprise regions composed of a material different than that of the surrounding body of elongate member 102. For example, in one embodiment, elongate member 102 may be made primarily of stainless steel while notches 200 may comprise regions of elongate member 102 made of a different material, for example an elastic compound. Notches 200 thus represent discontinuities in the material of the wall of elongate member 102, without necessarily changing the profile or thickness of elongate member 102.

Notches 200 may be operable to assist in directing a change in shape of elongate member 102 when force is applied to elongate member 102 through a pull-wire. In one such embodiment as described above, the application of tension to the pull-wire may apply force to an attachment point at distal tip 108, pulling the point in a proximal direction. As notches 200 may serve to locally increase the flexibility of elongate member 102, elongate member 102 may change shape to, for example, bend preferentially in the direction of notches 200 when tension is applied. Thus, in some embodiments, notches 200 may be shaped and positioned around elongate member 102 such that elongate member 102 will adopt a certain specific curve or series of curves when tension is applied to pull-wire 112.

In some embodiments of the present invention, and referring now to FIG. 3, an apparatus of the present invention may further comprise a handle 300 associated with proximal region 106 of elongate member 102. Handle 300 may be suitable for grasping and manipulating one or more of elongate member 102 and actuator 112, for example during insertion, positioning or guiding, and may, in some embodiments, be operable to facilitate a change in shape of elongate member 102. In some embodiments, handle 300 may comprise a housing 302, a first securing component 304 and a second securing component 306. Handle 300 may further comprise a means for connecting an energy source to one or more of elongate member 102, actuator 112 and any other electrical conductor operable to deliver energy to energy delivery component 110. For example, handle 300 may comprise an electrical connector for connecting to an energy source. In such embodiments, the electrical connector may be coupled to handle 300 via an electrical cable. Alternatively, as shown in FIG. 3B, actuator 112 may extend from a proximal end of handle 300 and may be operable to be electrically coupled to an energy source.

First securing component 304 may be operable to secure elongate member 102 while second securing component 306 may be operable to secure actuator 112. In the embodiment shown in FIGS. 3B-3D, second securing component 306 comprises a clamping apparatus operable to securely engage actuator 112. Actuation of handle 300 via, for example, button 310, may effect a change in the relative positions of first securing component 304 and second securing component 306, thus causing elongate member 102 and/or actuator 112 to move with respect to one another. Actuation of handle 300 may be achieved using any means for displacing a wire or similar component, including but not limited to one or more of a button, a knob and a switch. Actuation of handle 300 may involve the use of mechanical (including linear, rotational and other forces) and/or electrical energy and may be accomplished remotely. In some embodiments, handle 300 may optionally contain a ratcheting mechanism to maintain tension in actuator 112, for example by maintaining the position of one or more of first component 304 and second component 306 following actuation of handle 300. In some embodiments, handle 300 may be removable; for example, in one embodiment, first component 304 and second component 306 may be detachable from elongate member 102 and actuator 112, respectively. In such embodiments, handle 300 may further be re-attachable after being removed. Further, in such embodiments, handle 300 may additionally comprise one or more visual markers and/or one or more locks or other fastening mechanisms to aid in the positioning and attachment of first component 304 and second component 306 to elongate member 102 and actuator 112, respectively. Such markers and/or locks may be useful to orient the direction of bending of elongate member 102 with respect to handle 300, and to calibrate actuator 112 to the amount of tension already in the actuating mechanism. In embodiments comprising an actuator 112 that utilizes means other than tension to direct apparatus 100 in a desired direction, handle 300 may be operable to manipulate the actuator to effect the desired change in direction.

In accordance with embodiments of the present invention, any portion of elongate member 102, actuator 112, notches 200, energy delivery component 110 or insulating material 114 may comprise one or more markers. Such markers may include visual markers, tactile markers, radiopaque markers, radiolucent markers, or any other markers used to aid in the visualisation, localization, navigation, insertion, or detection of apparatus 100. Markers may be externally applied to a component, and may be of a variety of shapes and structures; they may be raised from the surface of a component or may conform to the surface of the component; they may be internal to a component. In some embodiments, components may be manufactured in whole or in part from materials that provide a visual or tactile distinction, thus acting themselves as markers. For example, in one embodiment, insulating material 114 may be manufactured from an radiopaque insulating material or from a material comprising radiopaque fillers. In another embodiment, one or more of elongate member 102, distal tip 108, energy delivery component 110 and actuator 112 may be plated with a radiopaque material, such as platinum or tungsten. In yet another embodiment, a radiopaque marker, such as a band, may be welded or otherwise attached to, for example, distal tip 108 or energy delivery component 110.

In further embodiments, as mentioned hereinabove, any or all of lumen 116, actuator 112 and notches 200 may not be present in the apparatus, in order, for example, to simplify the manufacturing process and make it more cost-effective. In addition, in such embodiments, the apparatus may have substantially similar mechanical properties when compared to a standard mechanical guide-wire.

Materials

In embodiments where elongate member 102 comprises an electrically conductive core wire, as described hereinabove, it may be made of a biocompatible metal or metal alloy, for example, including, but not limited to, stainless steel or Nitinol®. Actuator 112 may be conductive, and may, in some embodiments, have a high tensile strength, thus being able to tolerate the application of sufficient force to cause a change in shape of elongate member 102, when force is applied to actuator 112. An example of a material that may be suitable for actuator 112 is Nitinol®. Insulating material 114 may be composed from any material capable of providing electrical insulation, including, in some embodiments, Parylene or polytetrofluoroethylene (PTFE). Insulating material 114 may be applied to elongate member 102 by a variety of methods including, but not limited to: being overlain onto elongate member 102 and shrunk by the application of heat, being extruded over elongate member 102, and being sprayed or painted onto elongate member 102 in liquid form. Suitable materials for radiopaque markers or components include, but are not limited to, high-density metals such as platinum, iridium, gold, silver, tantalum, and tungsten or their alloys, or radiopaque polymeric compounds. Although the above materials are suggested as being suitable options for the manufacture of components of the present invention, the list is by no means meant to be limiting, and any other components with suitable properties may be used.

Method

In some embodiments, the present invention can be used to penetrate material in a patient's body. This penetration may be at least partially accomplished, in some embodiments, through the application of energy from an energy delivery component of an apparatus of the present invention, wherein the application of energy generates an electromagnetic field of sufficient density and sufficient power to generate sufficient heat in the material to vaporize the material. In addition, mechanical force applied to the distal tip of the apparatus may allow for penetration of softer material within the patient's body. Thus, a method of penetrating material may, in some embodiments, involve a combination of electrical penetration and mechanical penetration.

In one embodiment of a broad method aspect of the present invention, a treatment procedure may comprise the steps of: providing an electrosurgical apparatus, for example as described above; inserting the apparatus into a patient's body; guiding the device to a target site comprising material to be penetrated; positioning an energy delivery component adjacent the material; and delivering energy to penetrate at least a portion of the material. Further embodiments may comprise additional steps of, for example, manipulating an actuator, or otherwise guiding the apparatus through one or more of the patient's vasculature and the material being penetrated. In addition, as has been mentioned, penetration of the material may also be partially accomplished using mechanical energy to push through the material. This may be useful, for example, where the material is relatively soft.

Figure 4:
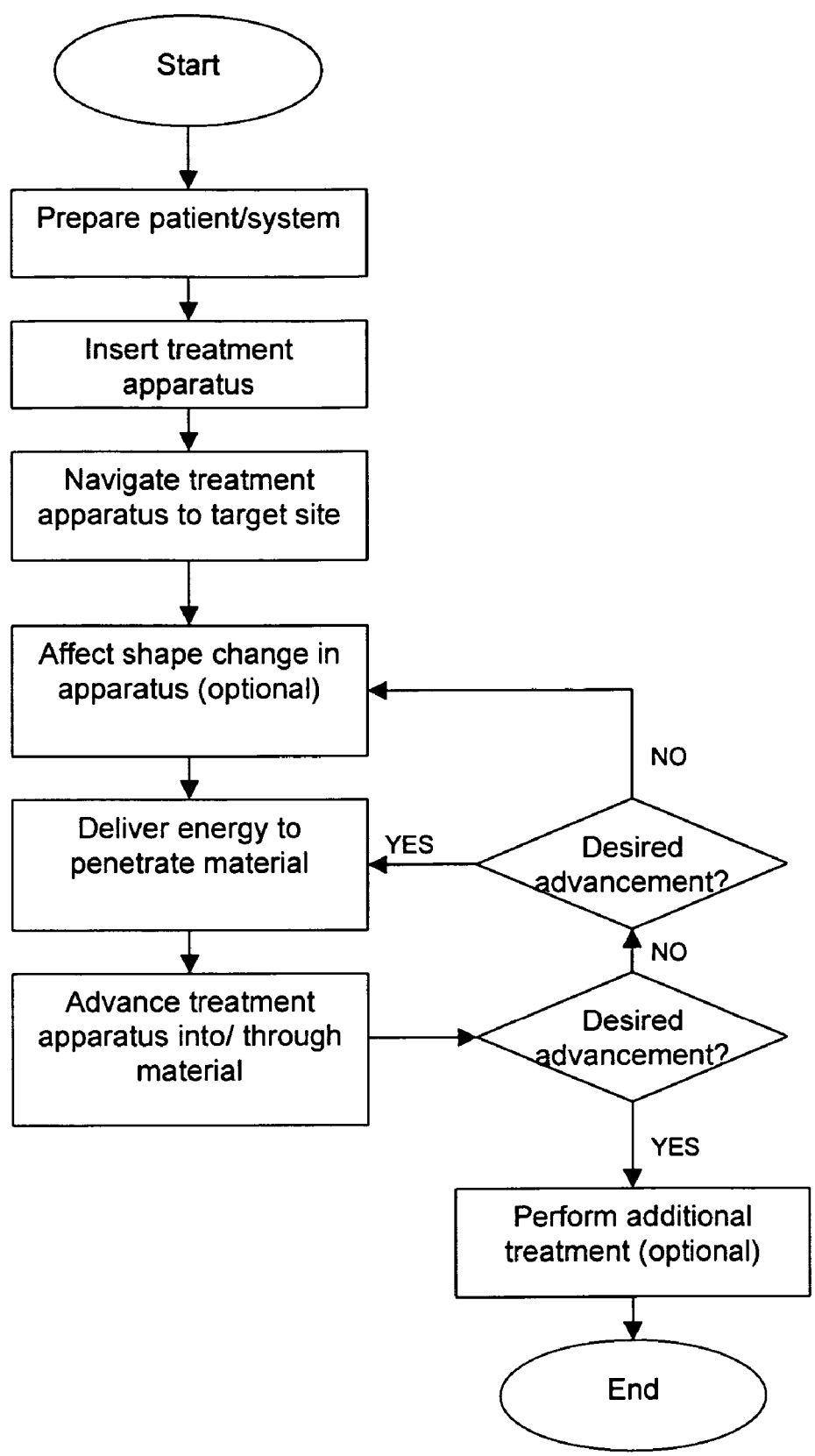
FIG. 4, in a flow chart, illustrates a method for creating a channel in accordance with an embodiment of the present invention.

In accordance with embodiments of the treatment method aspects of the present invention, the apparatus may be a component of a system including an energy source (such as, for example, the RFP-100 Baylis Medical RF Perforation Generator, manufactured by Baylis Medical Company Inc., Montreal, Canada), and a grounding pad or other return electrode, if operated in a monopolar mode. FIG. 4 illustrates, in flow-chart form, one embodiment of a treatment method of the present invention. This embodiment comprises: preparing a patient and system for treatment; inserting a treatment apparatus as described hereinabove into the vascular system of the patient; navigating the treatment apparatus through the vascular system to a target site; optionally effecting a change of shape, or otherwise reorienting the apparatus in order to position the energy delivery component adjacent at least a portion of the material to be penetrated; delivering energy via the apparatus to penetrate at least a portion of the material; advancing the apparatus into or through the material; and optionally performing another treatment or introducing another device at the site. The reader skilled in the art will readily appreciate that the patient may be a human or an animal.

The step of preparing a patient for treatment may include, but is not limited to one or more of: visualizing one or more treatment sites within the body of the patient using fluoroscopy, x-ray, contrast media, labeled markers such as radioactive compounds or solutions, using endoscopy procedures, using ultrasound, using Doppler imaging, or any other visualization method; characterizing the vascular system of the patient by measuring blood or serum levels of various compounds; measuring vascular pressure; and undertaking any other measuring or monitoring technique that may provide information that may be useable during any other step of the method. The step of preparing a system for treatment may include, but is not limited to one or more of: connecting a treatment apparatus, for example as described above, to an energy source; connecting a grounding pad or other return electrode to the energy source; attaching the grounding pad or return electrode to the patient; optionally passing the actuator through elongate member 102 (in some embodiments, the actuator may be permanently threaded through elongate member 102, thus obviating this step); optionally connecting the handle to the actuator and core wire (in some embodiments, the handle may be permanently connected to elongate member 102 and the actuator, thus obviating this step); and attaching one or more additional components to the treatment apparatus.

The step of navigating the treatment apparatus through the vascular system to a target site may additionally involve any of a variety of visualization techniques, including those techniques mentioned above for visualizing one or more treatment sites within the body of the patient. In one embodiment, the treatment apparatus may be furnished with one or more radiopaque markers, which may aid in the visualization of the treatment apparatus.

The step of effecting a change of shape in the apparatus in order to position the energy delivery component adjacent at least a portion of the material to be penetrated may be required if the means for navigating the treatment apparatus is not capable of sufficiently precise placement of the treatment apparatus. This step may, in one embodiment, be accomplished by effecting a change of shape in the distal end of an elongate member of the treatment apparatus. In one specific embodiment, such a change of shape is affected by the creation of tension in a pull-wire attached to elongate member 102; for example, if the pull-wire were attached to the distal tip of elongate member 102, the application of force to the proximal end of the pull-wire may create a tension in the pull-wire, which may result in force being applied to the distal end of elongate member 102. In some embodiments where elongate member 102 has one or more notches associated with a distal region thereof, the application of force to the distal end may cause elongate member 102 to change shape. Alternatively, for example if at least a portion of the elongate member is curved, torque may be applied to the proximal region of the apparatus in order to orient the distal end in a desired direction.

The step of delivering energy may be preceded by an optional step of measuring or sensing the composition of the material to be penetrated. For example, in one embodiment, the treatment apparatus may be used as part of an impedance monitor to determine the impedance of the material to be penetrated. The impedance value thus measured may then be compared to known impedance values of various materials in order to determine the composition of the material to be penetrated. Alternatively, the apparatus may include a pressure sensor operatively coupled to the distal region of the apparatus distal for measuring a pressure at the distal end of the apparatus. In such embodiments, the pressure measurement may indicate the composition of the material to be penetrated. In one particular embodiment, the composition of the material to be penetrated may indicate the use of a specific form of energy to penetrate the material. For example, if the material is determined to be relatively soft, mechanical energy, in other words the exertion of a pressure by the distal region 108, may be employed, while if the material is determined to be relatively hard, electrical energy may be employed.

The step of delivering energy via the treatment apparatus to penetrate at least a portion of the material may involve, in one embodiment, delivering an electromagnetic signal (for example a signal in the radiofrequency (RF) range) to the material from the energy source via the apparatus. In one specific embodiment, the RF signal may have a frequency in the range of from about 300 kHz to about 1 MHz, and more specifically, in very specific embodiments of the invention, of from about 460 kHz to about 500 kHz, and may be delivered with a power of at least about 5 W at a voltage of at least about 75 Volts (peak-to-peak). In some embodiments, the step of delivering energy may, in addition, involve delivering mechanical energy to push through softer material, for example, within a hard portion of an occlusion.

The step of advancing the treatment apparatus into or through the material may involve one or both of movement of the treatment apparatus as a whole, or reorienting at least a portion of the treatment apparatus, as described above with respect to positioning the distal tip of elongate member 102. Following the step of advancing the treatment apparatus, the step of reorienting the treatment apparatus and/or the step of delivering energy via the treatment apparatus may be repeated one or more times.

The optional step of performing another treatment or introducing another device at the site may involve, in some embodiments, introducing a balloon catheter to the site, overtop of the treatment apparatus; introducing a stent or other supporting structure to the site overtop of or through the treatment apparatus; delivering a pharmaceutical compound to the site; delivering energy to create a lesion or coagulate tissue or fluid in the vicinity of the site; introducing embolic coils; placing an IVUS probe for visualization; or adding or removing any other material to or from the site. In addition, this step may further comprise removal and possible re-attachment of the handle of the apparatus, in order to allow for the introduction of another device to the treatment site.

Applications

An embodiment of a treatment method of the present invention may be useful, for example, to penetrate through a material at least partly occluding a vessel of a body of a patient in order to recannalize the vessel. In such an example, the material to be penetrated may comprise a vascular occlusion having regions of various degrees of toughness and calcification. Thus, this particular application may benefit from utilizing electrical energy in conjunction with the mechanical application of pressure in order to penetrate and traverse the occlusion.

Figure 5:
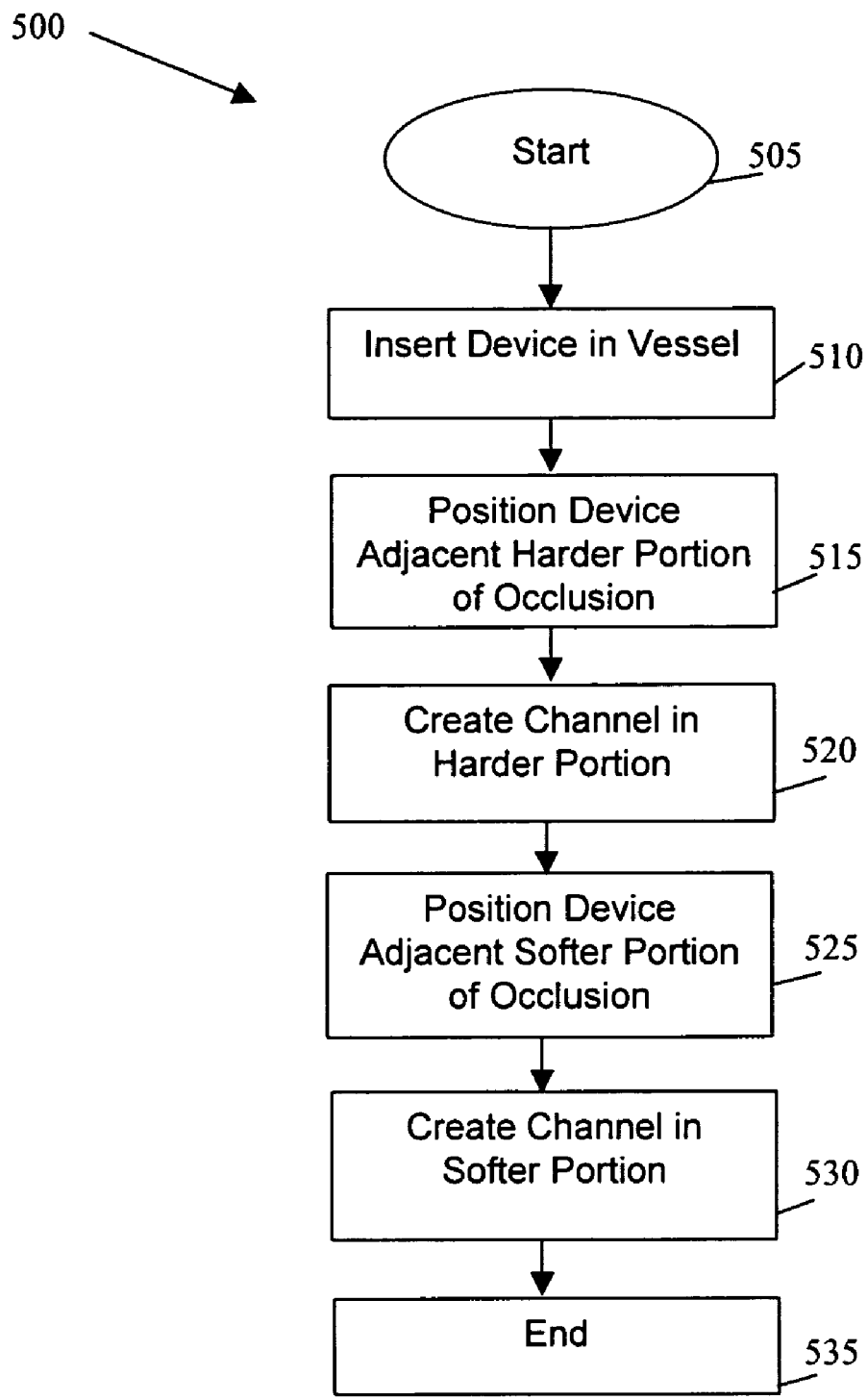
FIG. 5, in a flow chart, illustrates a method for creating a channel in accordance with another embodiment of the present invention.
Figure 6:
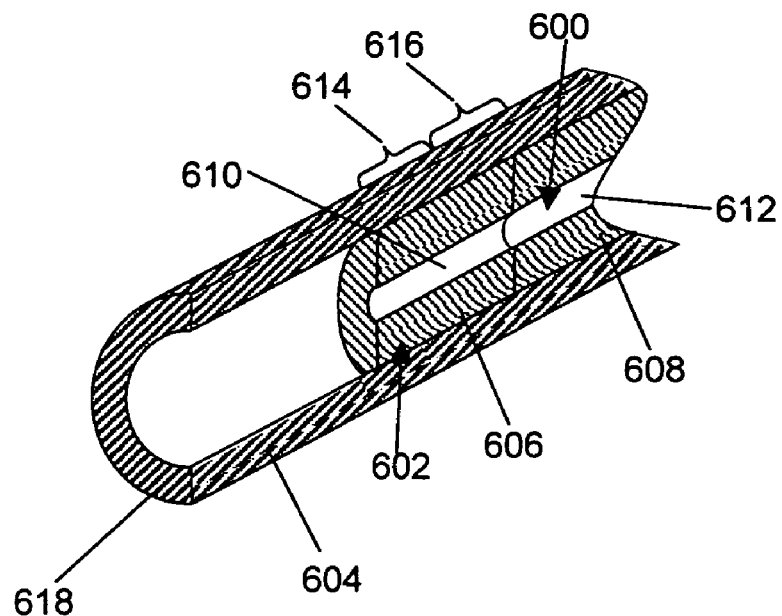
FIG. 6, in a perspective view, illustrates the channel created in an occlusion of a body vessel using the method illustrated in FIG. 5.

Referring to FIGS. 5 and 6, in a more specific example of implementation, the present invention is embodied in a method 500 for creating a channel 600 through an occlusion 602 located in a substantially elongated body vessel 604 of a patient, the occlusion 602 including an occlusion harder portion 606 extending substantially longitudinally relative to the body vessel 604 and an occlusion softer portion 608 extending substantially longitudinally relative to, the body vessel 602, the occlusion softer portion 608 being located substantially adjacent to and substantially coaxially with the occlusion harder portion 606. Also, it should be noted that for the purposed of this example and of the appended claims, the term body vessel applied to any suitable body structure defining a lumen, such as for example a blood vessel, a bile duct, an airway, and various tubes and/or ducts associated with the digestive system, the urinary tract and/or the reproductive system, among other possibilities.

For example, it has been found that the proposed method is well suited to the creation of channels through plaque partially or totally occluding a blood vessel. Such occlusions often have harder portions, for example end caps thereof, and located substantially adjacent softer portions, for example the portion of the occlusion located between the end caps.

Also, the person skilled in the art will readily appreciate that the channel 600 is not necessarily a self-supporting channel 600. Therefore, in some embodiments of the invention, the channel 600 is further dilated or receives a stent, or is both dilated and receives a stent, after having been created.

The method 500 use a channel creating apparatus, such as, for example, an embodiment of the apparatus described hereinabove, defining an apparatus distal end portion, such as for example the distal tip described hereinabove, insertable into the body vessel 600. The channel creating apparatus includes an energy delivery component operatively coupled to the apparatus distal end portion for delivering energy substantially adjacent the apparatus distal end portion.

The method 500 starts at step 505. Then, at step 510, the apparatus distal end portion is inserted into the body vessel 604.

Afterwards, at step 515, the apparatus distal end portion is positioned substantially adjacent the occlusion harder portion 606 and, at step 520, a channel first portion 610 of the channel 600 is created through the occlusion harder section 606. Creating the channel first portion 610 includes delivering the energy into the occlusion harder portion 606.

Subsequently, at step 525, the apparatus distal end portion is positioned substantially adjacent the occlusion softer portion 608 and, at step 530, a channel second portion 612 of the channel 600 is created through the occlusion softer portion 608 by pushing the apparatus distal end portion through at least a portion of the occlusion softer portion 608, the channel second portion 612 being created substantially without using the energy delivery component to deliver energy into the occlusion softer portion 608. For example, the apparatus distal end portion is pushed by applying a substantially longitudinal force to an apparatus proximal portion (for example, the proximal region of the apparatus described hereinabove) longitudinally opposed to the apparatus distal end portion. In another example, the apparatus distal end portion is pushed directly, for example using a motor or any other actuator coupled to the apparatus distal end portion.

It should be noted that while embodiments of the apparatus described hereinabove are usable to perform the method 500, in other embodiments of the invention, any suitable apparatus may be used Also, while in the method 500 the channel first portion 610 is created before the channel second portion 612, it is within the scope of the invention to create the channel second portion 612 before the channel first portion 610.

It has been found that the method embodied in FIGS. 5 and 6 leads to a new and unexpected result in which the channel 600 is created relatively easily and relatively safely through both the occlusion harder and softer portions 606 and 608 using the same apparatus. In addition, channel 600 may be created by an apparatus whose mechanical properties are substantially similar to those of standard mechanical guide-wires. Other advantages of the proposed methods have been mentioned hereinabove.

In some embodiments of the invention, the occlusion harder portion 606 has a hardness that is substantially too large to allow pushing the apparatus distal end portion through the occlusion harder portion 606 without delivering the energy into the occlusion harder portion 606. For example, it was found that when the occlusion harder portions 606 has a hardness such that a mechanical pressure of at least about 20 kg/cm$^2$ is required to create a channel thereinto, conventional mechanical guide-wires are typically unusable to create the channel first portion 610. These embodiments of the present invention thus provide a means for traversing an occlusion that standard mechanical guide-wires may be unable to penetrate.

In some embodiments of the invention, step 520 is performed as follows. First, a channel first portion first segment 614 is created through the occlusion harder portion 606 while delivering the energy into the occlusion harder portion 606 and the apparatus distal end portion is advanced through the channel first portion first segment 614. The advancement of the apparatus distal end portion may be simultaneous with or subsequent to the delivery of energy. When the channel first portion first segment 614 has been created, the delivery of energy is stopped. Afterwards, a user of the channel creating apparatus may attempt to push the apparatus distal end portion through the occlusion 602 substantially without delivering energy via the energy delivery component. Upon the apparatus distal end portion being unable to be pushed through the occlusion 602 after having created the channel first portion first segment 614, a channel first portion second segment 616 extending from the channel first portion first segment 614 is created similarly to the channel first portion first segment 614. If required, additional segments of the channel first portion 610 are also similarly created. If the apparatus distal end portion can be pushed through the occlusion 602, the creation of the channel 600 continues as described with respect to the creation of the channel second portion 612.

Therefore, by repeatedly testing for the possibility of creating the channel mechanically after, for example, each energy delivery step, an intended user may lower the risk that the energy delivered may injure tissues that should remain intact, such as for example the vessel wall 618 of the body vessel 604.

In some embodiments of the invention, the energy is delivered for a predetermined amount of time before stopping the delivery of the energy. In other embodiments, the user may decide, during the course of the procedure, on the amount of time during which energy should be delivered. For example, the amount of time during which energy may be delivered may be from about 0.1 seconds to about 5 seconds. In a more specific embodiment of the invention, the amount of time during which energy is delivered for a duration of from about 0.5 second to about 3 seconds. It has been found that these amounts of time allow for the creation of the channel 600 in a reasonable amount of time while reducing the risk of unwanted injuries. During the periods of time described above, the energy may be delivered continuously or as a pulsed waveform.

In other embodiments of the invention, when performing step 520, the intended user assesses continuously, periodically or intermittently the position of the apparatus distal end portion relatively to the occlusion softer portion 608. Upon detection that the apparatus distal end portion is located substantially adjacent the occlusion softer portion 608, the delivery of the energy is stopped and the channel second portion 612 is created. For example, the position of the apparatus distal end portion is assessed using a position assessment method selected from the group consisting of an imaging technique, an impedance measurement, a measurement of a force exerted onto the apparatus distal end portion, a measurement of a pressure exerted onto the apparatus distal end portion and a measurement based on ultrasonic signals, among other possibilities.

In these embodiments, assessing the position of the apparatus distal end portion may allow the user to deliver energy to the occlusion 602 over a minimal duration, which again may lower the risk of injuring structures adjacent to the occlusion 602.

In some embodiments, if a user is unable to mechanically advance the apparatus through the occlusion softer portion, the user may choose to deliver energy via the energy delivery component or may attempt to re-orient at least a portion of the apparatus. As described hereinabove, such re-orientation may take the form of steering the device in some manner or, alternatively, applying torque to a portion of the device. In some such embodiments, the position of the apparatus may be assessed, as described hereinabove, prior to choosing which course of action to follow.

In some particular situations, an occlusion may comprise another, relatively hard, portion, for example on the opposite end of the first hard portion. In such embodiments, a channel third portion may be created through this hard portion of the occlusion in substantially the same manner as the channel first portion, described hereinabove.

As mentioned hereinabove, the energy delivered may be any suitable energy. For example, the energy may be radio-frequency electromagnetic energy or radiant energy, for example laser light, among other possibilities. When radio-frequency energy is used, it has been found that radio-frequency energy delivered with a power of at least about 5 W at a voltage of at least about 75 Volts (peak-to-peak) produces good channel creation performances while remaining relatively safe for the patient. Also, the use of radio-frequency energy is advantageous as it allows the use of relatively small apparatus distal end portions that are relatively robust, and which therefore are relatively well suited to the creation of the channel second portion 612 using mechanical forces.

Figure 7:
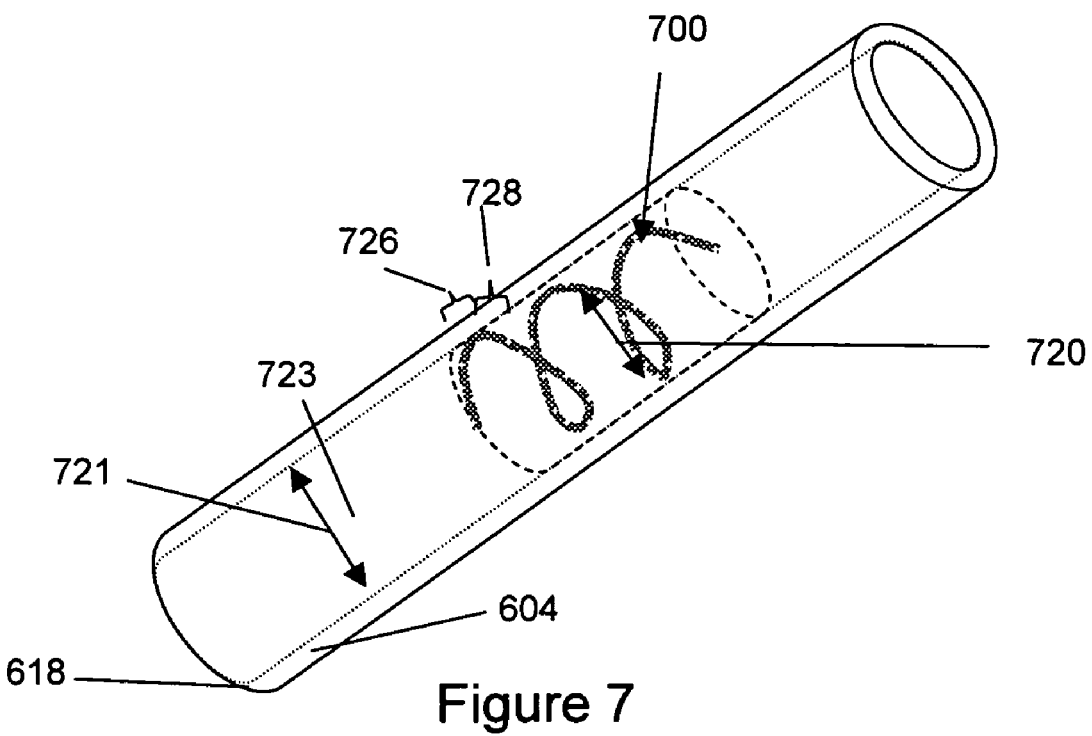
FIG. 7, in a perspective view, illustrates an alternative channel created in an occlusion of a body vessel using the method in FIG. 5.

While the channel 600 is substantially rectilinear, it is within the scope of the invention to create channels having any other suitable shape. For example, it has been found that having channels in which at least the first channel portion is substantially helical, and as such defines a helix axis extending substantially longitudinally relatively to the body vessel, is particularly effective in certain situations. Indeed, as further described hereinbelow, these channels may be created by operating the channel creating apparatus such that the energy is delivered primarily in a direction leading substantially away from the vessel wall 618. This type of energy delivery minimizes the risks of injury to the vessel wall 618. FIG. 7 illustrates such a substantially helical channel 700. Typically, the channel 700 is created such that at least a portion of the energy is delivered into said occlusion 602 in a direction leading substantially longitudinally away from the apparatus distal end portion. In other words, the energy is delivered at least in part forwardly from the apparatus distal end portion at location in which the apparatus distal end portion is to be advanced.

Channel 700, in some embodiments, has a helix diameter 720 of from about 50 percent to about 90 percent of a diameter 721 of the lumen 723 of the body vessel 604. Also, these channels typically, but not exclusively, have a pitch of from about 3 millimeters to about 3 centimeters.

More specifically, these channels 700 may be created using channel creating apparatuses wherein the apparatus distal end portion defines a substantially rectilinear section and a substantially curved section extending substantially longitudinally from the substantially rectilinear section. For example, the curved section may be formed by temporarily deforming the apparatus distal end portion, as described hereinabove. Alternatively, the curved section may be permanently or semi-permanently formed into the apparatus distal end portion. In some embodiments, the curved section defines an apparatus distal end.

Creating the channel first portion then includes orienting the apparatus distal end substantially away from the vessel wall 604, delivering the energy into the occlusion harder portion 606 to create a channel first portion first segment 726, advancing the apparatus distal end into the channel first portion first segment 726 and reorienting the apparatus distal end substantially away from the vessel wall 604. After having reoriented the apparatus distal end, the energy is once again delivered into the occlusion harder portion 606 to create a channel first portion second segment 728.

In such embodiments, when the distal end portion is re-oriented during the creation of channel 600, energy may be delivered via the energy delivery component, even in the occlusion softer portion 608, in order to facilitate the re-orientation of the distal end portion.

In some embodiments of the invention, the energy delivery component is selectively operable in an energy delivering state and a deactivated state. In the energy delivering state, the energy is delivered substantially adjacent the apparatus distal end portion. In the deactivated state, the energy is substantially not delivered substantially adjacent the apparatus distal end portion.

When such an energy delivery component is used, the method 500 may be performed such that the channel first portion 610 is created through the occlusion harder section

606 by operating the energy delivery component in the energy delivering state and delivering the energy into the occlusion harder portion 606. The channel second portion 612 is created through the occlusion softer portion 608 by operating the energy delivery component in the deactivated state and pushing the apparatus distal end portion through at least a portion of the occlusion softer portion 608.

An advantageous, but non-limiting, embodiment of the invention using such an energy delivery component is one wherein the channel creating apparatus includes a pressure sensor operatively coupled to the apparatus distal end portion for measuring a pressure exerted onto the occlusion by the apparatus distal end portion. Then, in some embodiments of the invention, the method 500 includes operating the energy delivery component in the energy delivering state if the measured pressure is substantially above a predetermined pressure and operating the energy delivery component in the deactivated state if the measured pressure is substantially below the predetermined pressure. The predetermined pressure is, for example, the pressure at which mechanical penetration is difficult or impossible. The energy delivery is manually switched on or off, or the channel creating apparatus includes a controller for automatically turning the energy delivering apparatus to the deactivated state if the pressure exerted onto the occlusion by the apparatus distal end portion is substantially below the predetermined pressure and turning the energy delivery apparatus to the energy delivering state if the pressure exerted onto the occlusion by the apparatus distal end portion is substantially above a predetermined pressure.

In these embodiments, the activation of energy delivery occurs only if the energy is required to create the channel 600 or a portion thereof. Otherwise, only a mechanical force is used to create the channel 600. This reduces uncertainty and variability in the manner in which the method is performed. Also, by reducing or eliminating the need to repeatedly test for the possibility of creating the channel mechanically, the method may be performed relatively fast with relatively low risks of injuring the patient.

In some embodiments of the invention, if an intended user is unable to push the apparatus distal end portion through the occlusion softer portion 608, the intended user may reorient the apparatus distal end portion within the occlusion softer portion 608 and attempt to push the apparatus distal end portion through the occlusion softer portion 608 substantially without delivering energy via the energy delivery component. However, in some embodiments of the invention, energy is used to facilitate the reorientation of the apparatus distal end portion.

In any or all of the embodiments described herein, a user may elect to initially use a standard mechanical guide-wire to attempt to penetrate an occlusion. Once a hard portion of the occlusion is encountered, the method 500 as described hereinabove may be employed.

EXAMPLE

A clinician was presented with an 83-year-old male for left leg intervention. Access was gained on the left side for an antegrade approach down the leg. Angiograms revealed a totally occluded anterior tibial vessel. The clinician elected to recanalize it. He gained access to the proximal portion of the occlusion with a 0.035" Spectranetics® Quick-Cross catheter, which he uses often. He then asked for a straight tipped PowerWire™ RF Guidewire (a commercial embodiment of an apparatus of the present invention) that he used to access the occlusion through the Quick-Cross catheter. At a setting of 10 W and 2 seconds RF energy was applied. After this first application of energy the clinician stated "it's going through it!" A second burst of energy was then administered. At this point approximately 4 cm of the occlusion had been crossed. The clinician then used the PowerWire mechanically to further recanalize the vessel. By the time he finished using the PowerWire in this manner, he had traversed between 30 and 40 cm of lesion and was in the dorsalis pedis artery at the level of the metatarsals. The clinician proceeded to balloon dilate the dorsalis pedis and anterior tibial arteries over top of a 0.014 Asahi wire and was surprised to find some blood flow through these vessels after he had finished.

In a further application of the treatment method of the present invention, the material to be penetrated may be a vessel wall of a patient's vasculature. In such an embodiment, energy may be delivered in order to penetrate the vessel wall in order to, for example, bypass a vascular occlusion. The penetration of the vessel wall may be complete, wherein the entire wall thickness is penetrated, or it may be partial, thus creating a channel into, but not through, the vessel wall. This treatment method may be useful in cases where the occluding material may not be able to be readily penetrated by the delivery of energy. Thus, rather than attempting to penetrate the occlusion, a bypass may be created by removing material from the vessel wall to create a channel around the occluding material.

The methods of the present invention may also be useful in other applications, including but not limited to transeptal procedures, arterial-venous shunts, the treatment of various cardiac disorders or conditions and, in general, wherever material in a patient's body should be penetrated.

Many other methods and particular applications may be used with an apparatus of the present invention, and some embodiments of the method of the present invention may be used with an apparatus other than that specifically described in the "APPARATUS" section of this application.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the present invention has been described hereinabove by way of preferred embodiments thereof, it can be modified, without departing from the spirit and nature of the subject invention as defined in the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A method for creating a channel through an occlusion located in a substantially elongated body vessel of a patient, said occlusion including an occlusion harder portion extending substantially longitudinally relatively to said body vessel and an occlusion softer portion extending substantially longitudinally relatively to said body vessel, said occlusion softer portion being located substantially adjacent to and substantially coaxially with said occlusion harder portion, said occlusion harder portion being substantially harder than said occlusion softer portion, said method using a channel creating apparatus defining an apparatus distal end portion insertable into said body vessel, said channel creating apparatus including an energy delivery component operatively coupled to said apparatus distal end portion for delivering energy substantially adjacent said apparatus distal end portion, said method comprising:

inserting said apparatus distal end portion into said body vessel;

positioning said apparatus distal end portion substantially adjacent said occlusion harder portion, and creating a channel first portion through said occlusion harder portion by delivering said energy into said occlusion harder portion using said energy delivery component;

determining if said apparatus distal end portion is located adjacent said occlusion softer portion by attempting to push said apparatus distal end portion through said occlusion substantially without delivering energy using said energy delivery component; and upon said apparatus distal end portion being able to be pushed through said occlusion, creating a channel second portion through said occlusion softer portion by pushing said apparatus distal end portion through at least a portion of said occlusion softer portion, substantially without using said energy delivery component to deliver energy into said occlusion softer portion.

2. A method as defined in claim 1, wherein creating said channel first portion includes:

creating a channel first portion first segment through said occlusion harder portion by delivering said energy into said occlusion harder portion using said energy delivery component;

advancing said apparatus distal end portion through said channel first portion first segment;

stopping the delivery of said energy after creating said channel first portion first segment; and after advancing said apparatus distal end portion through said channel first portion first segment, attempting to push said apparatus distal end portion through said occlusion substantially without delivering energy using said energy delivery component.

3. A method as defined in claim 2, further comprising, upon said apparatus distal end portion being unable to be pushed through said occlusion after having created said channel first portion first segment, creating a channel first portion second segment substantially extending from said channel first portion first segment by delivering said energy into said occlusion using said energy delivery component.

4. A method as defined in claim 2, wherein said energy is delivered for a predetermined amount of time before stopping the delivery of said energy.

5. A method as defined in claim 4, wherein said predetermined amount of time is from about 0.1 seconds to about 5 seconds.

6. A method as defined in claim 1, further comprising, upon said apparatus distal end portion being unable to be pushed further through said occlusion softer portion, reorienting said apparatus distal end portion within said occlusion softer portion and attempting to push said apparatus distal end portion through said occlusion softer portion substantially without delivering energy via said energy delivery component.

7. A method as defined in claim 1, further comprising, upon said apparatus distal end portion being unable to be pushed further through said occlusion softer portion, creating a channel third portion by delivering said energy into said occlusion using said energy delivery component.

8. A method as defined in claim 1, wherein said channel first portion is created before said channel second portion, said method further comprising assessing the position of said apparatus distal end portion relative to said occlusion softer portion; and upon said apparatus distal end portion being located substantially adjacent said occlusion softer portion, stopping the delivery of said energy.

9. A method as defined in claim 8, wherein said position of said apparatus distal end portion is assessed using a position assessment method selected from the group consisting of an impedance measurement, a measurement of a force exerted onto said apparatus distal end portion, a measurement of a pressure exerted onto said apparatus distal end portion, a measurement based on ultrasonic signals and an imaging technique.

10. A method as defined in claim 1, wherein delivering said energy includes delivering radio-frequency energy.

11. A method as defined in claim 1, wherein said channel first portion is substantially helical and defines a helix axis extending substantially longitudinally relatively to said body vessel.

12. A method as defined in claim 11, wherein said channel first portion defines an helix diameter, said helix diameter being from about 50 percent to about 90 percent of a diameter of a lumen of said body vessel.

13. A method as defined in claim 11, wherein said channel first portion defines a pitch, said pitch being from about 3 millimeters to about 3 centimeters.

14. A method as defined in claim 1, wherein said body vessel includes a vessel wall;

said apparatus distal end portion defines a substantially rectilinear section and a substantially curved section extending substantially longitudinally from said substantially rectilinear section;

said substantially curved section defines an apparatus distal end; and creating said channel first portion includes:

orienting said apparatus distal end substantially away from said vessel wall;

delivering said energy into said occlusion harder portion to create a channel first portion first segment;

advancing said apparatus distal end into said channel first portion first segment and reorienting said apparatus distal end substantially away from said vessel wall;

after having reoriented said apparatus distal end, delivering said energy into said occlusion harder portion to create a channel first portion second segment.

15. A method as defined in claim 1, wherein said body vessel is a body vessel selected from the group consisting of a blood vessel, a bile duct and an airway.

16. A method as defined in claim 1, wherein said occlusion harder portion has a hardness that is substantially too large to allow pushing said apparatus distal end portion through said occlusion harder portion without delivering said energy into said occlusion harder portion.

17. A method as defined in claim 1, wherein delivering said energy includes delivering at least a portion of said energy into said occlusion in a direction leading substantially longitudinally away from said apparatus distal end portion.

18. A method as defined in claim 1, wherein said occlusion harder portion has a hardness such that a mechanical pressure of at least about 22 kg/cm$^2$ is required to create a channel thereinto substantially without delivering energy.

19. A method for creating a channel through an occlusion located in a substantially elongated body vessel of a patient, said occlusion including an occlusion harder portion extending substantially longitudinally relatively to said body vessel and an occlusion softer portion extending substantially longitudinally relative to said body vessel, said occlusion softer portion being located substantially adjacent to and substantially coaxial with said occlusion harder portion, said method using a channel creating apparatus defining an apparatus distal end portion insertable into said body vessel, said channel creating apparatus including an energy delivery component operatively coupled to said apparatus distal end portion for delivering energy substantially adjacent said apparatus distal end portion, said energy delivery component being selectively operable in an energy delivering state and a deactivated state, wherein in said energy delivering state, said energy is delivered substantially adjacent said apparatus distal end portion, and in said deactivated state, said energy is substantially not delivered substantially adjacent said apparatus distal end portion, said method comprising:

- inserting said apparatus distal end portion into said body vessel:
- positioning said apparatus distal end portion substantially adjacent said occlusion harder portion and creating a channel first portion through said occlusion harder portion by operating said energy delivery component in said energy delivering state and delivering said energy into said occlusion harder portion using said energy delivery component;
- determining if said apparatus distal end portion is located adjacent said occlusion softer portion by attempting to push said apparatus distal end portion through said occlusion substantially without delivering energy using said energy delivery component; and
- upon said apparatus distal end portion being able to be pushed through said occlusion, creating a channel second portion through said occlusion softer portion by operating said energy delivery component in said deactivated state and substantially simultaneously pushing said apparatus distal end portion through at least a portion of said occlusion softer portion.

20. A method as defined in claim 19, wherein said channel creating apparatus includes a pressure sensor operatively coupled to said apparatus distal end portion for measuring a pressure exerted onto said occlusion by said apparatus distal end portion, said method further comprising:

- operating said energy delivery component in said energy delivering state if said measured pressure is substantially above a predetermined pressure; and
- operating said energy delivery component in said deactivated state if said measured pressure is substantially below said predetermined pressure.

* * * * *